(12) United States Patent
Kang et al.

(10) Patent No.: US 7,470,404 B2
(45) Date of Patent: Dec. 30, 2008

(54) FLUID SAMPLE COLLECTION AND ISOLATION CUP

(75) Inventors: Jemo Kang, Princeton, NJ (US); Kyung-ah Kim, Princeton, NJ (US); Arthur Weber, Whitehouse Station, NJ (US); In Jung Kim, West Windsor, NJ (US); Larry Porter, Princeton, NJ (US); Won Bae Yoon, Plainsboro, NJ (US)

(73) Assignee: Princeton Biomeditech Corporation, Princeton, NJ (US)

( * ) Notice: Subject to any disclaimer, the term of this patent is extended or adjusted under 35 U.S.C. 154(b) by 1110 days.

(21) Appl. No.: 10/751,797

(22) Filed: Jan. 5, 2004

(65) Prior Publication Data

US 2004/0136877 A1 Jul. 15, 2004

Related U.S. Application Data

(63) Continuation of application No. 09/918,288, filed on Jul. 30, 2001, now Pat. No. 6,680,027.

(51) Int. Cl.
*G01N 33/00* (2006.01)
(52) U.S. Cl. .................... 422/102; 422/50; 422/55; 422/56; 422/57; 422/58; 422/68.1; 422/99; 422/100; 422/103
(58) Field of Classification Search ............... 422/50, 422/55, 56, 57, 58, 68.1, 99, 100, 102, 103
See application file for complete search history.

(56) References Cited

U.S. PATENT DOCUMENTS 6,680,027 B2 * 1/2004 Kang et al. ............... 422/58

* cited by examiner

*Primary Examiner*—Sam P Siefke
(74) *Attorney, Agent, or Firm*—Fox Rothschild LLP; Gerard P. Norton; Vyacheslav Vasilyev

(57) ABSTRACT

A collection and testing cup for fluid characterization is disclosed. The cup has a lid assembly with a tamper evident closure; a cylinder that extends into the fluid in the collection cup, also with a tamper evident closure; a piston with a conduit and one-way valve through which a portion of the fluid can be forced into an isolation chamber separate from the main collection cup for testing. The lid assembly cylinder is configured with an aperture or passage near the bottom of the cylinder to allow a small portion of fluid to enter the lower portion of the cylinder from the collection cup chamber and a piston with a central conduit and valve initially positioned near the top of the cylinder adjacent to the lid. The piston, when pushed down the cylinder, closes the aperture communicating with collection cup chamber and forces a predetermined volume of fluid from the lower portion of the cylinder through the conduit and valve to the upper portion of the cylinder, isolating a portion of the fluid sample from the fluid in the collection cup chamber. The valve prevents the fluid from returning to the lower portion of the cylinder and to the collection cup chamber. A testing device may be inserted into the fluid sample at the upper portion of the piston for characterization of one or more analytes in the fluid sample.

14 Claims, 8 Drawing Sheets

FLUID SAMPLE COLLECTION AND ISOLATION CUP

BACKGROUND OF THE INVENTION

The present invention relates to an apparatus for collecting and isolating a fluid specimen, and more particularly to a cup which can be used to receive, transport and store a fluid specimen as well as to provide an isolated sample for a fluid characterization testing.

Many tests are conducted to characterize the component or detect certain components or compounds of interest in fluids from the environment or body fluids. For example, employers sometimes test urine samples of prospective employees to determine whether the individual abuses controlled substances such as illegal drugs. Generally, a fluid sample is collected in an open mouth jar, and then closed and transported to the testing location. Several types of devices have been designed to collect uncontaminated urine such as the devices disclosed in U.S. Pat. Nos. 4,040,791; 4,393,881: 4,557,274; 4,569,090 and 5,797,855.

After a sample is collected, it is important to maintain the integrity of the sample until the time of testing. Adulteration of the collected fluid should be prevented to ensure an accurate test result. To prevent adulteration after collection, the cup contents should be maintained in a securely sealed, uncontaminated state.

In the testing of a fluid sample, most collection cups require opening the collection cup lid and transferring a small amount of the sample for testing. Many fluids being tested such as body fluids are considered to be potentially infectious and should be handled with proper caution. The test operator and/or surroundings can be contaminated and infected during transfer by contact with or spilling the sample fluid. Furthermore, the collected fluid sample itself can be contaminated by the surroundings and thereby lose its integrity. When the sample is transferred and tested, the identity of the sample can be confused with others, resulting in an uncertain conclusion. Therefore, it would be desirable if the test can be performed without transferring the sample fluid from the original collection cup.

U.S. Pat. Nos. 3,980,436; 4,385,115; 4,827,944; 4,960,130; 5,016,644; 5,038,793; 5,077,012; 5,215,102; 5,283,038; 5,368,583 and 5,403,551 disclose the introduction of test strips or other test devices into a specimen collection device in a general sense. These devices permit the testing of a sample without requiring transfer of the sample out of the collection device. However, some of these devices present problems with mechanism for communicating the sample to the test strips or they cannot ensure that at least a portion of the original sample remains isolated from the initial testing, since the test strip or test device is not isolated from the main body of collected fluid and consequently contamination from the test device is not eliminated.

It is highly desirable that the integrity of a fluid sample be maintained for later use of the sample, especially in the case of testing of urine for the presence of drugs. The collected urine sample must generally be kept until a confirmation test is later performed.

U.S. Pat. Nos. 4,976,923; 5,119,830 and 5,591,401 disclose in general terms urine collection cups that have a test strip on the lid. In these devices, it is typically necessary to invert the cup in order for the sample to be contacted with the test strip and spilling of the sample fluid can occur if the lid is not tightly closed. The collection cup in U.S. Pat. No. 5,976,895 can be used to collect and test urine in the same cup. However, the specimen is not divided into two portions prior to testing and contamination of the specimen from, for example, the test strip can occur.

Thus, there is a need for a fluid collection cup that is easy to use and prevents contamination from both laboratory technician and collected fluid by preventing contact of one with the other. Second, there is a need for a fluid collection cup that can be transported without spilling the sample and that is protected from tampering after collection. Third, there is a need for a fluid collection cup that can preserve collected fluid in a secure, intact state until the time of a confirmation test.

These and other features and objects of the invention will be more fully understood from the following detailed description of the preferred embodiments which should be read in light of the accompanying drawings.

SUMMARY OF THE INVENTION

This invention is a fluid sample collection and isolation device that has a secure locking system and a sample isolating cylinder that has a tamper evident locking system. The sample isolating cylinder separates a fraction of the fluid, for testing, from the main fluid in the collection cup. Using this fluid collection and isolation device, sample transfer to a separate vessel for testing is not required and the integrity of the collected fluid for further confirmation testing is maintained.

The apparatus for collecting a fluid specimen has a collection chamber with a sidewall and bottom for receiving a fluid specimen. It also has a fluid isolation assembly comprising a cylinder means having an interior sidewall, an upper portion and a lower portion and a piston slidably disposed within the cylinder means and in contacting relationship with the interior sidewall. A passage communicates between the collection chamber and the interior of the cylinder means and the passage is positioned to permit at least a portion of said fluid specimen to enter the lower portion of the cylinder means. A conduit communicates between the lower portion of the cylinder means and a isolation chamber. Preferably, the isolation chamber is formed by the sidewall of the cylinder and the top of the piston. The conduit is disposed to transfer the portion of the fluid specimen from the lower portion of the cylinder means to the isolation chamber when the piston is moved from the upper portion towards the lower portion of the cylinder means. Preferably, a one-way valve is disposed within the conduit to prevent fluid from returning from the isolation chamber into the lower portion of the cylinder means.

In a preferred embodiment, the collection cup has the usual shape of a cup and lid, but an isolation cylinder is attached to the center of the lid. The lid has a locking system that works in conjunction with the base container so that once the lid is closed, it cannot be opened without cutting the tamper evident locking system. In the isolation cylinder, a piston is installed, which functions to isolate the fluid for testing in the upper portion of the isolation cylinder. Once the cylinder tamper evident seal is broken and the cylinder lid is removed, the piston is pressed with a stick test device or other plunger means so that the fluid below the piston is forced up through a conduit in the piston and forms an isolation chamber in the upper portion of the cylinder. The fluid in the isolation chamber is used for testing for specific analytes. The piston is designed with a one-way valve to prevent back flow of the fluid once it goes into the upper portion. Therefore, the fluid in the isolation chamber is isolated completely from the portion of the sample remaining in the collection cup or base container. The fluid in the collection cup remains intact, without any contamination, before, during and after testing.

The top of the isolation cylinder has a cap with a slot, into which the test device is introduced. A typical stick-type test device can be used to press against the piston and move it towards the bottom of the isolation cylinder. Another lid with a locking device may be placed over the isolation cylinder to prevent tampering before testing and replaced after use to prevent spilling of the fluid above the piston in the isolation chamber. To control the fluid volume into the isolation chamber, there is a space below the piston in the lower portion of the isolation cylinder. There is at least one aperture in the isolation cylinder wall positioned above this lower portion to allow fluid from the collection cup to flow into the bottom of the cylinder. Only the volume of fluid that fills the space below the aperture is pumped above the piston. When the piston is moved to the bottom of the isolation cylinder, it also serves to block the opening and prevents fluid from returning to the collection cup.

In a preferred embodiment, the cup has a lid assembly with a tamper evident closure; a cylinder that extends into the fluid in the collection cup, also with a tamper evident closure; a piston with a conduit and one-way valve through which a portion of the fluid can be forced into an isolation chamber separate from the main collection cup for testing. The lid assembly cylinder is configured with an aperture near the bottom of the cylinder to allow a small portion of fluid to enter the lower portion of the cylinder from the collection cup chamber and a piston with a central conduit and valve initially positioned near the top of the cylinder adjacent to the lid. The piston, when pushed down the cylinder, closes the aperture communicating with collection cup chamber and forces a predetermined volume of fluid from the lower portion of the cylinder through the conduit and valve to the upper portion of the cylinder, isolating a portion of the fluid sample from the fluid in the collection cup chamber. The valve prevents the fluid from returning to the lower portion of the cylinder and to the collection cup chamber. A testing device may be inserted into the fluid sample at the upper portion of the piston for characterization of one or more analytes in the fluid sample.

BRIEF DESCRIPTION OF THE DRAWINGS

The accompanying drawings, which are incorporated in and form a part of the specification, illustrate the embodiments of the present invention and, together with the description serve to explain the principles of the invention.

In the drawings.

DETAILED DESCRIPTION OF PREFERRED EMBODIMENTS

Figure 1:
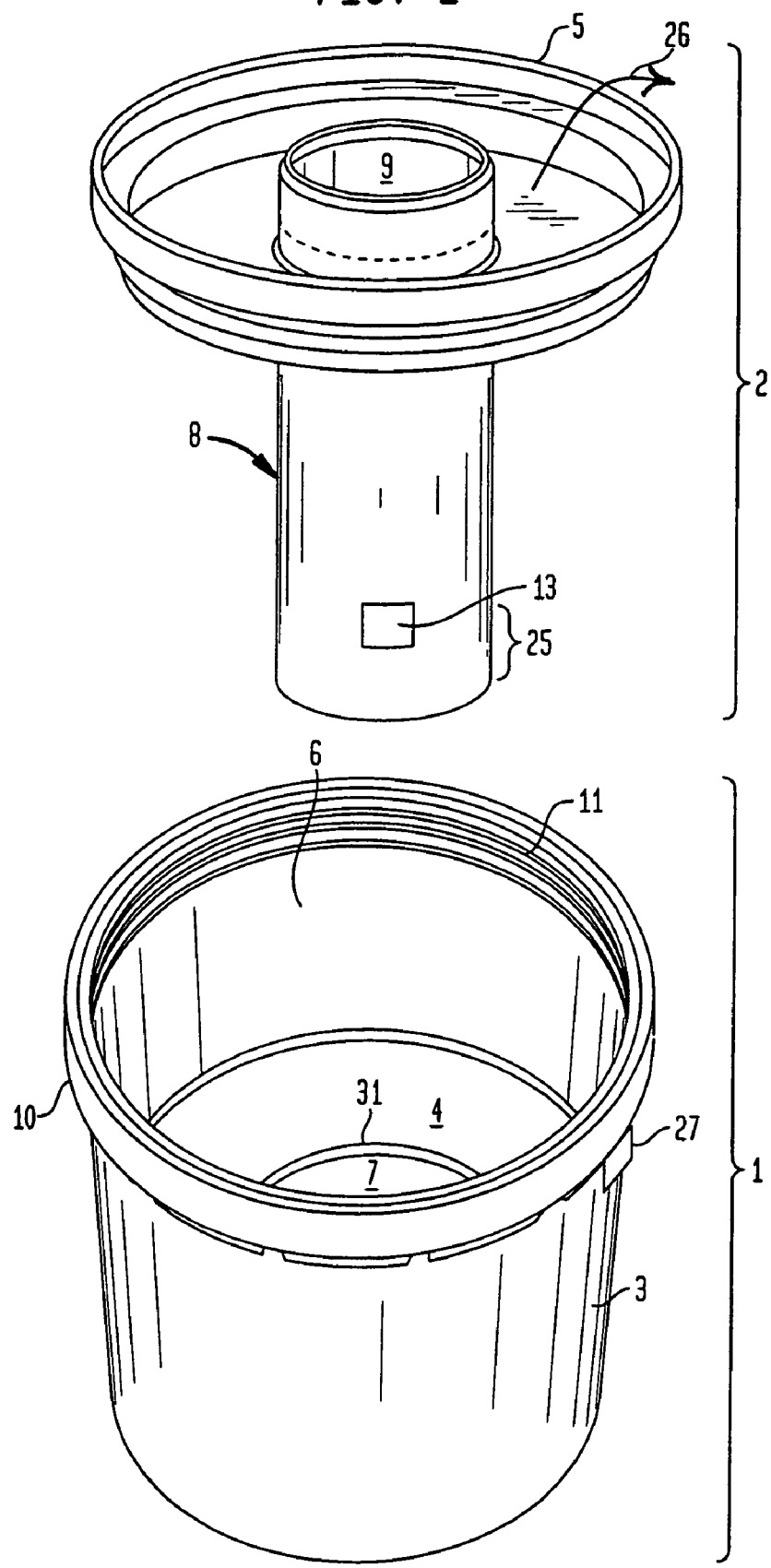
FIG. 1 is an exploded perspective view of a fluid collection and testing device according to the present invention.

In describing a preferred embodiment of the invention illustrated in the drawings, specific terminology will be used for the sake of clarity. However, the invention is not intended to be limited to the specific terms so selected, and it is to be understood that each specific term includes all technical equivalents which operate in a similar manner to accomplish a similar purpose.

Figure 2:
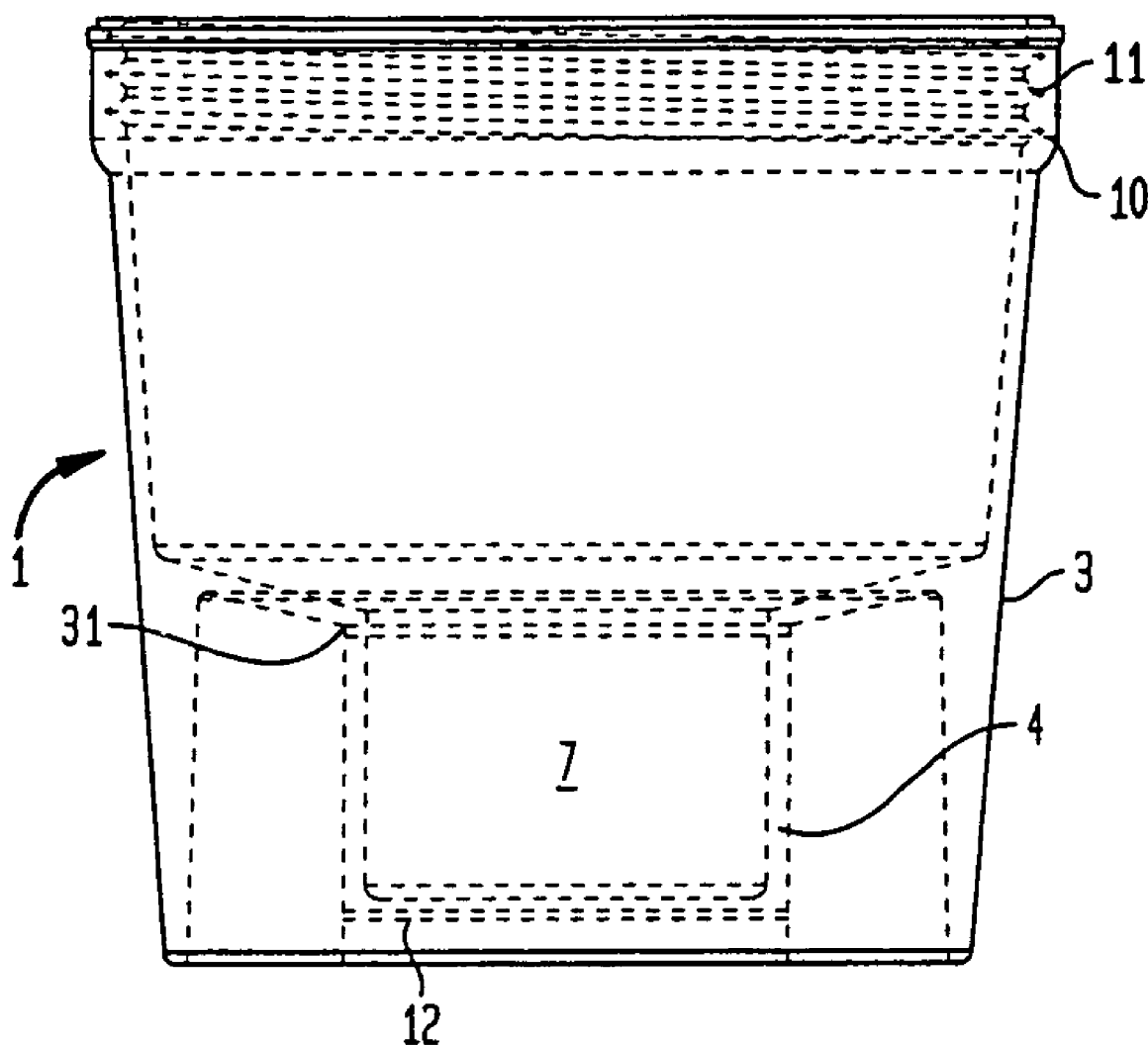
FIG. 2 is a perspective side view of a collection cup portion of the device.
Figure 3:
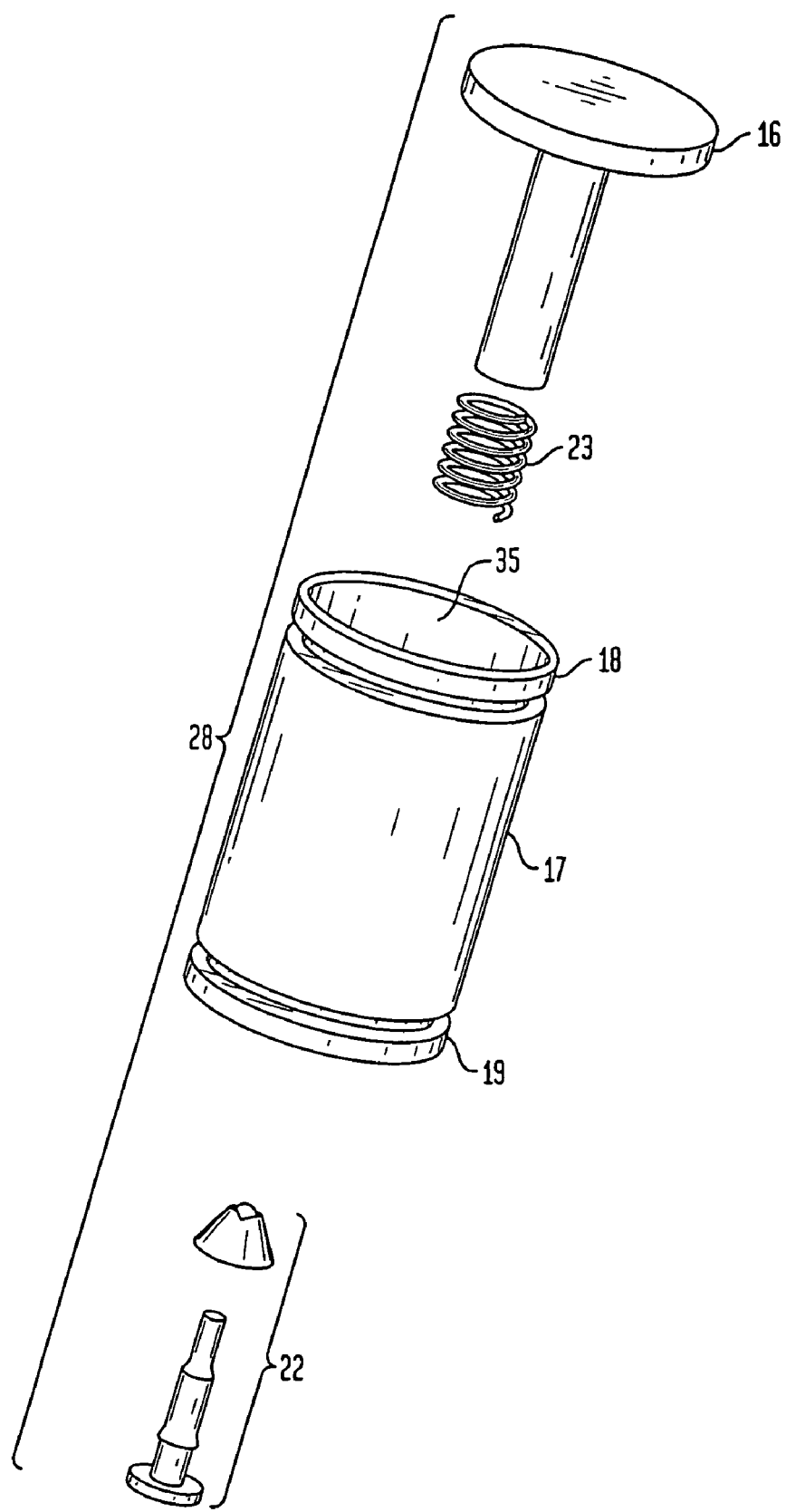
FIG. 3 is an exploded perspective view of the piston.
Figure 4:
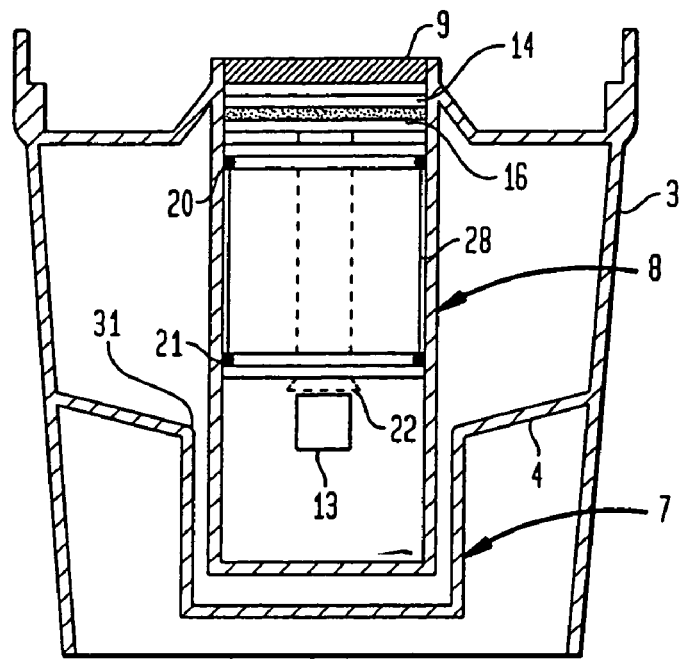
FIG. 4 is a sectional side view of the device along a along a plane passing the longitudinal axis through the center of the device from top to bottom illustrating the piston before it has been moved to the lower portion of the isolation cylinder.
Figure 5:
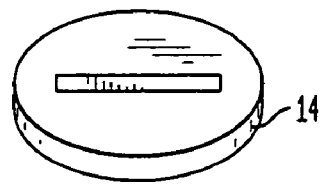
FIG. 5 is a perspective view of the inner cap of the isolation cylinder having a slot for inserting an analyte test stick.
Figure 6:
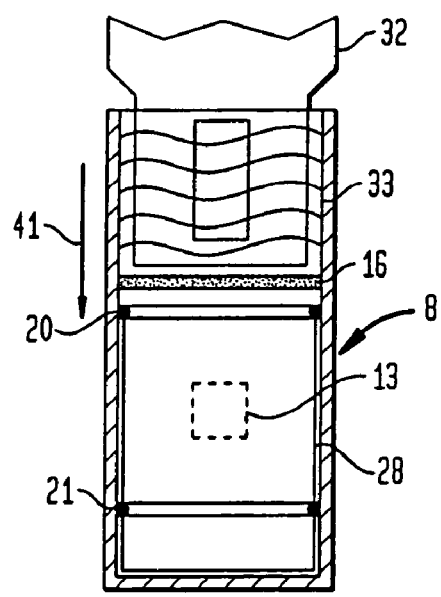
FIG. 6 is a sectional side view of the isolation cylinder and piston through a plane passing through the central, longitudinal axis of the isolation cylinder illustrating the piston positioned in the lower portion of the isolation cylinder.
Figure 7:
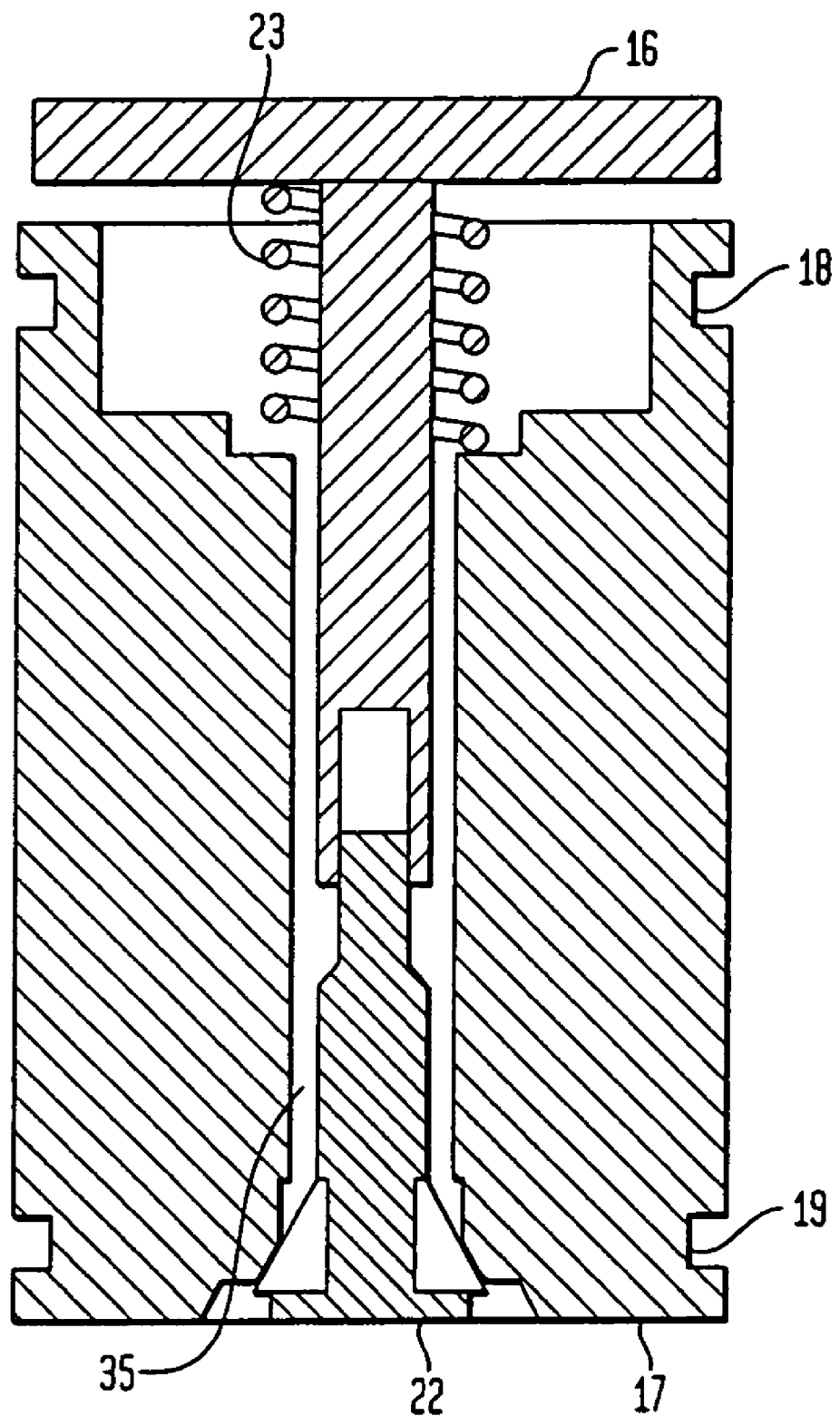
FIG. 7 is sectional side view of the piston through a plane passing through the central, longitudinal axis of the piston illustrating the conduit and valve in a closed position.
Figure 8:
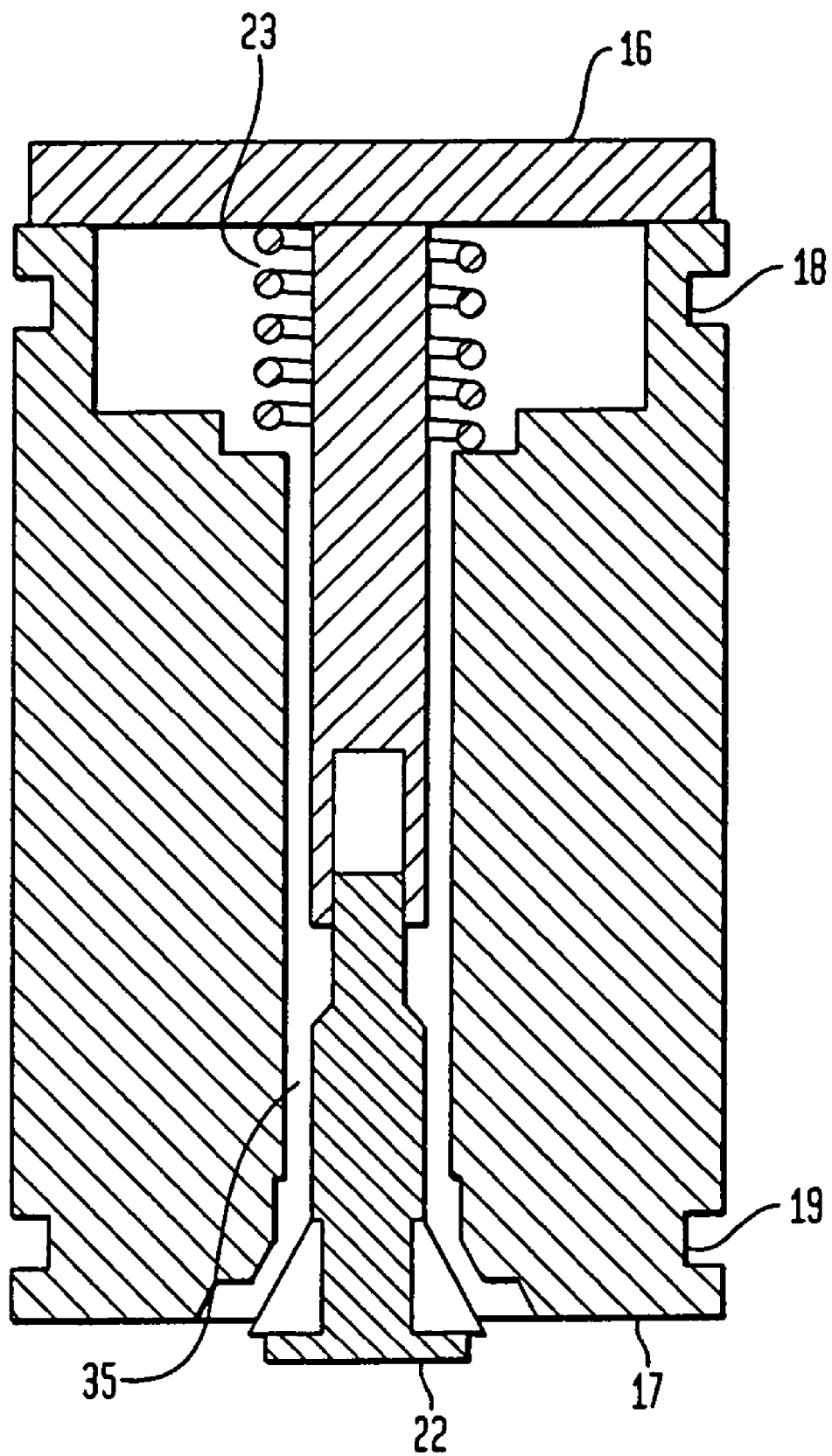
FIG. 8 is sectional side view of the piston through a plane passing through the central, longitudinal axis of the piston illustrating the conduit and valve in an open position.
Figure 9:
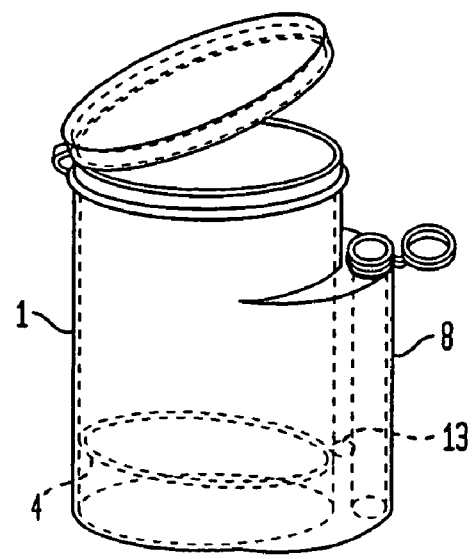
FIG. 9 is a perspective view of the device illustrating an embodiment where the isolation cylinder positioned along the exterior wall of the collection chamber.
Figure 10:
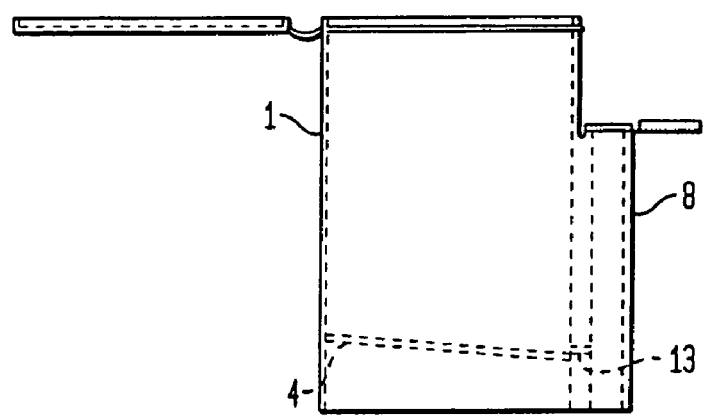
FIG. 10 is a side view of the embodiment illustrated in FIG. 9.
Figure 11:
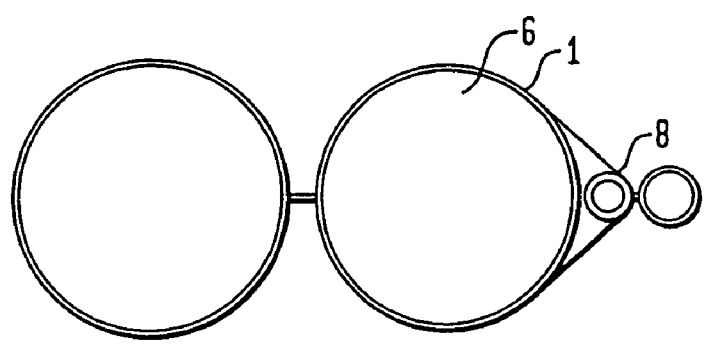
FIG. 11 is a top view of the embodiment illustrated in FIG. 9.
Figure 12:
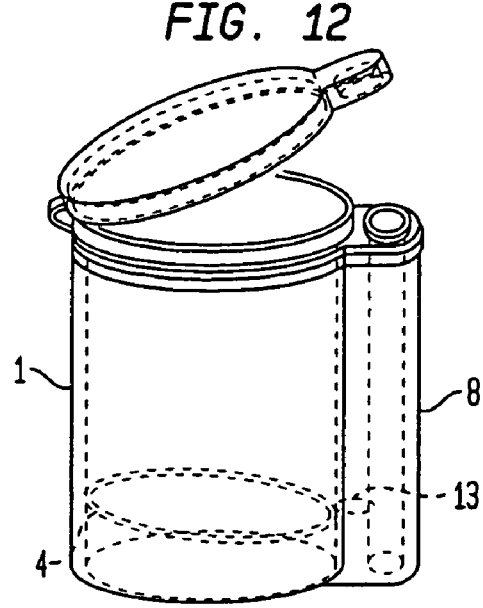
FIG. 12 is a perspective view of the device illustrating an alternative embodiment where the isolation cylinder positioned along the exterior wall of the collection chamber.
Figure 13:
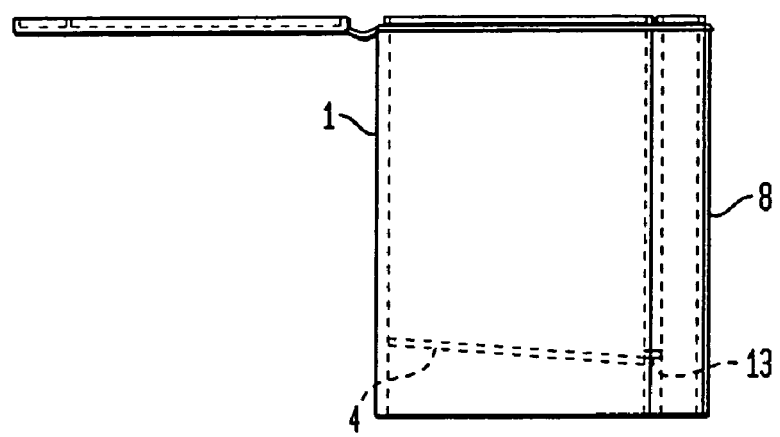
FIG. 13 is a side view of the embodiment illustrated in FIG. 12.
Figure 14:
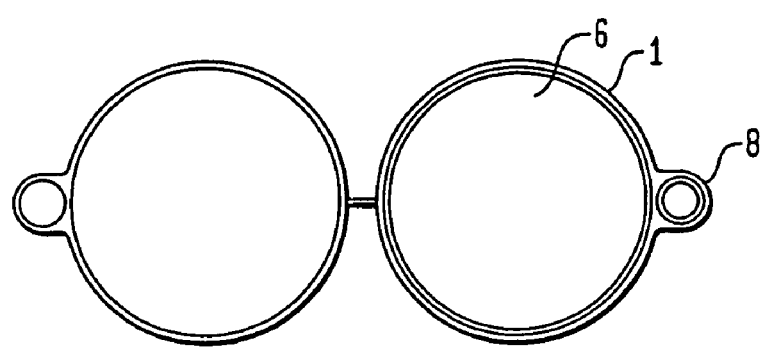
FIG. 14 is a top view of the embodiment illustrated in FIG. 12.

With reference to the drawings, in general, and FIGS. 1 through 14 in particular, the apparatus of the present invention is disclosed.

The fluid collection and testing device is made of two parts, a base container 1 and a lid and fluid isolation assembly 2. The base container 2 is cup-like, having a cylindrical or squarish sidewall 3, a closed bottom 4 and a top opening 6. The sidewall 3 may have a slight taper or be straight. The bottom 4 of the cup has an reservoir 7 for the purpose of minimizing the required amount of fluid to be collected. The reservoir 7 has a diameter or size sufficient to allow the lower portion 25 (below the opening 13) of the isolation cylinder 8 to be seated when the base container is closed completely with the lid 2. The bottom 4 has an angle and is inclined into reservoir 7 which thereby filled with fluid even if only a small amount of fluid is collected in the cup. A typical collection container may have a capacity of about 180 ml and minimum of 50 ml of fluid required for a test. However, the present invention is not intended to be limited to this size or capacity.

The rim of the outside of the reservoir 7 of bottom 4 has a shallow sidewall 12 to meet and rest upon the cap 9 of additional cups for safe and convenient stacking. The top of the base container has a circumferential rib 10 to provide rigidity to the container and screw threads 11 formed into the container proximate opening 6 sized to accept a lid 5. When mating threads on lid 5 are interengaged onto threads 11, this provides a means for sealing the opening 6 in a fluid-tight relationship. Other means of fluid-tight attachment such as a snap-on friction fit may also be used as long as such means securely hold the lid onto the cup.

A secure locking device is preferably attached on the lid. Any suitable tamper resistant or tamper evidence mechanisms as are well known in the art may be used. In a preferred embodiment, a plastic thread with arrow shaped end 26 is used. Along the rim of the base container 1, a receptacle 27 for the arrow 26 is disposed. After closing the lid 5 on base container 1 the arrow tip is inserted into the receptacle on the rim. To open the lid 5, the thread must be cut. Once arrow 26 is inserted in receptacle 27, it cannot be removed without cutting the string.

The lid and fluid isolation assembly 2 has an isolation cylinder 8 in the center of lid 5. The location of the isolation cylinder is not restricted to the middle of the lid. It can be located any place in or outside on the base container or lid as long as the fluid in the base container is communicable through passage 13 to isolation cylinder 8. The top of the isolation cylinder preferably has a tamper protective cover cap 9 and the bottom of the cylinder is closed. The cap 9 prevents contamination of the isolation cylinder before the test and spilling of urine from the isolation chamber 33 after the test. The cap preferably remains closed until the time of the test, is opened by twisting at the time of testing, and is closed again after testing for safe, clean and convenient transport. The isolation cylinder protrudes downward from the lid 5. The isolation cylinder 8 is placed in the base container 1 when the lid is closed.

The isolation cylinder 8 has an opening 13. One or more openings may be used. Opening 13 allows fluid to enter the isolation cylinder 8 when the cylinder is inserted into the base container 1, i.e., when the lid is closed. The size of the cylinder opening 13 is preferably large enough for fluid in the base container to enter the isolation cylinder easily without interference from surface tension. There are preferably at least two openings 13 so that any trapped air can exit easily. When the lid 2 is closed, the lower edge of the openings 13 are located at the same or slightly above the level of the top edge 31 of the reservoir 7, so that collected fluid right above the reservoir flows freely into the isolation cylinder through the unblocked cylinder openings 13.

Below the cap 9, another cap 14 is located. Cap 14 has a slot 15 in its middle in which test stick device 32 may be inserted. The purpose of this cap 14 is to prevent exposure of the fluid to the operator while testing occurs and to support the test device 32 while it is being inserted. The slot 15 is sized to fit the test stick devices as are commonly used and commercially available for testing for the presence of analytes in fluids. The edge of the slot 15 is preferably lined with a soft flexible plastic to wipe off excess fluid from the test device 32 when the test device is withdrawn from the isolation chamber 33 above piston 28 after the test. One skilled in the art will recognize that commercial available chemical immunoassay test strips (without the rigid test stick device) may also be inserted in slot 15.

Alternatively, isolation chamber 33 may remain sealed and a slot may be fabricated in collection cup 1, for example in lid 5, in which a test strip or test stick may be inserted to conduct an analysis of the fluid specimen. In this embodiment, it would be desirable to have a separate plunger mechanism to move cylinder 28 towards the bottom of isolation cylinder 8.

A piston 28 is located in the upper portion of isolation cylinder 8, under the cap 14, and extends in length to just above the openings 13. The piston consists of a press plate 16, a piston body 17, O-rings 20 and 21, a piston valve 22 and spring 23. Mounted around the piston body in annular channels 18 and 19 cut into the exterior surface of the body 17 are respectively an upper O-ring, 20 and lower O-ring 21. These O-rings 20 and 21 slideably engage in a contacting relationship and form a fluid seal against the interior sidewall of the isolation cylinder 8; i.e., seal the contact area between the piston and the inner sidewall of the cylinder 8. The O-rings prevent the flow of fluid in the isolation cylinder except through conduit 35 in the center of the piston body 17. This conduit is the only means of passage of fluid from below the piston 28 to the isolation chamber 33 above the piston in the isolation cylinder 8. This conduit 35 is kept closed by the valve 22 located at the bottom of the piston body 17 until the piston press plate 16 is pressed.

The illustrated embodiment shows conduit 35 routed through piston body 17. However, it is contemplated that the conduit could be routed along other paths such as those exterior to the isolation cylinder 8 or along a sidewall of isolation cylinder 8. The essential requirement is that the conduit opening in the lower portion of cylinder be below the lower surface of piston and the apertures 13. Also, it is contemplated that an isolation chamber located separate or exterior to cylinder 8 may be used.

When the press plate 16 is pressed by a plunger such as a test stick device through the slot 15, the piston 28 moves downwardly in the direction of arrow 41 towards the bottom of isolation cylinder 8. Valve 22 is opened allowing the fluid below the piston to flow through conduit 35 up above the piston into isolation chamber 33. At this point, the fluid may be absorbed into the absorbent pad of a typical test stick device and a test is performed. Any kind of test stick device can be used as long as it can press the piston.

One advantage of this embodiment is that collection and sample isolation is separated from the choice of fluid test. The analyte test strips are not embedded or housed in the device. This provides additional advantages. Any desired fluid test may be conducted with the same collection device depending on the needs of the user. There is also no need to specially package the device in desiccant packaging which can be cumbersome and may add substantial additional cost to the product. The test strips are maintained in the typical foil and plastic packaging.

The fluid volume or depth in the isolation chamber 33 for a fluid test is controlled to fit a test device by the length of the lower portion 25 of the isolation cylinder 8 and the size (and therefore volume) of the conduit 35. When the base container 1 is firmly closed with the lid and fluid isolation assembly 2 after fluid collection, a certain amount of pressure is built inside the container. This pressure pushes fluid into the piston conduit 35 when the valve 22 of the piston 28 is opened. Therefore, when piston 28 is pressed all the way down, the volume of fluid that flows through the opened valve is (1) the amount of fluid going up through the opened valve until the outside pressure of the collection cup is equal to the pressure inside of the collection cup plus (2) the amount of fluid going up through the opened valve due to the volume displaced due to movement of the piston. As the size of the conduit 35 and the length of the lower portion 25 of the isolation cylinder 8 are increased, the amount of fluid pumped up into isolation chamber 33 is increased.

The fluid sample collection and isolation device of the present invention may be fabricated from any suitable materials such as glass, metal or preferably plastics. Thermoplastics such as polypropylene and polycarbonate are preferred.

Although there has been hereinabove described a fluid sample collection and isolation device in accordance with the present invention, for the purposes of illustrating the manner in which the invention may be used to advantage, it should be appreciated that the invention is not limited thereto. Accordingly, any and all modifications, variations, or equivalent arrangements which may occur to one skilled in the art should be considered to be within the scope of the present invention as defined in the appended claims.

What is claimed is:

1. An apparatus for collecting a fluid specimen comprising:
   a collection chamber having a sidewall and bottom for receiving a fluid specimen;
   a fluid isolation assembly comprising
   a cylinder means having an interior sidewall, an upper portion and a lower portion,
   a piston slidably disposed within the interior of the cylinder means and in contacting relationship with the interior sidewall, a passage communicating between said collection chamber and the interior said cylinder means, said passage positioned to permit at least a portion of said fluid specimen to enter the lower portion of the cylinder means;

a conduit communicating between the lower portion of the cylinder means and an isolation chamber, said conduit disposed to transfer said portion of said fluid specimen from the lower portion of the cylinder means to the isolation chamber when said piston is moved from the upper portion towards the lower portion of the cylinder means; and a valve mounted on the piston and positioned between the lower portion of the cylinder means and the isolation chamber for preventing fluid from flowing from the isolation chamber to the lower portion of the cylinder means.

2. The apparatus of claim 1 comprising:

a closure means for preventing said portion of the fluid specimen from flowing from the interior of the cylinder means to the collection chamber.

3. The apparatus of claim 1, wherein said passage comprises an opening on the interior sidewall and said piston covers the opening when the piston is slidably moved towards the lower portion of the cylinder means.

4. The apparatus of claim 1, wherein said conduit passes through the piston.

5. The apparatus of claim 1, wherein the isolation chamber is formed of the interior sidewall of the upper portion of the cylinder means and the piston.

6. The apparatus of claim 1 further comprising:

a collection chamber closure means disposed above the collection chamber sidewall.

7. The apparatus of claim 6, wherein the collection chamber closure means comprises means for detecting evidence of removal the closure means from the collection chamber sidewall.

8. The apparatus of claim 6, wherein the fluid isolation assembly is integrally connected to the collection chamber closure means.

9. The apparatus of claim 1, wherein the fluid isolation assembly further comprises:

a cylinder closure means disposed above the upper portion of the cylinder means.

10. The apparatus of claim 9, wherein the cylinder closure means comprises means for detecting evidence of removal of the closure means from the upper portion of the cylinder means.

11. The apparatus of claim 9, wherein the cylinder closure means comprises an opening for inserting a fluid test strip into the upper portion of the cylinder means.

12. The apparatus of claim 9, wherein the cylinder closure means comprises an opening for inserting a means for moving the piston towards the lower portion of the cylinder means.

13. The apparatus of claim 1, wherein the collection chamber comprises a reservoir for collecting the fluid specimen disposed in the bottom of collection chamber.

14. The apparatus of claim 13, wherein the reservoir is adapted to receive the lower portion of the cylinder means.

* * * * *